US009615723B2

(12) United States Patent
Umemoto

(10) Patent No.: US 9,615,723 B2
(45) Date of Patent: Apr. 11, 2017

(54) INSERTION APPARATUS

(71) Applicant: OLYMPUS CORPORATION, Tokyo (JP)

(72) Inventor: Yoshitaka Umemoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 60 days.

(21) Appl. No.: 14/318,845

(22) Filed: Jun. 30, 2014

(65) Prior Publication Data

US 2014/0316201 A1   Oct. 23, 2014

Related U.S. Application Data

(63) Continuation of application No. PCT/JP2013/068188, filed on Jul. 2, 2013.

(30) Foreign Application Priority Data

Jul. 10, 2012   (JP) ................ 2012-154629

(51) Int. Cl.
*A61B 1/01* (2006.01)
*A61B 1/00* (2006.01)
*G02B 23/24* (2006.01)

(52) U.S. Cl.
CPC ........ *A61B 1/00006* (2013.01); *A61B 1/0016* (2013.01); *A61B 1/00025* (2013.01);
(Continued)

(58) Field of Classification Search
CPC ... A61B 1/00154; A61B 1/051; A61B 1/0669; A61B 1/0676; A61B 2017/00278; A61B 2017/00292
See application file for complete search history.

(56) References Cited

U.S. PATENT DOCUMENTS 8,235,942 B2 *   8/2012   Frassica ........... A61B 17/12099
                                                              600/101
8,784,302 B2 *   7/2014   Moriyama ......... A61B 1/00073
                                                              600/106
(Continued)

FOREIGN PATENT DOCUMENTS

CN         1933761 A      3/2007
JP       2005-319121 A   11/2005
(Continued)

OTHER PUBLICATIONS

Chinese Office Action dated Sep. 15, 2015 from related Chinese Patent Application No. 201380007546.3, together with an English language translation.

(Continued)

*Primary Examiner* — John P Leubecker
*Assistant Examiner* — Rajaa El Alami
(74) *Attorney, Agent, or Firm* — Scully, Scott, Murphy & Presser, P.C.

(57) ABSTRACT

An insertion apparatus includes a first drive control section controlling a drive state of a drive member in such a manner that a rotary unit rotates toward a first periaxial direction with a first rotation amount during a reference time. The insertion apparatus includes a second drive control section controlling the drive state of the drive member in such a manner that the rotary unit rotates toward a second periaxial direction with a second rotation amount smaller than the first rotation amount during the reference time.

10 Claims, 12 Drawing Sheets

(52) U.S. Cl.
CPC ...... *A61B 1/00135* (2013.01); *A61B 1/00147* (2013.01); *A61B 1/00154* (2013.01); *A61B 1/01* (2013.01); *G02B 23/2476* (2013.01)

(56) References Cited

U.S. PATENT DOCUMENTS

| | | | | |
|---|---|---|---|---|
| 8,939,898 | B2* | 1/2015 | Omoto | A61B 1/00006 600/114 |
| 2005/0272976 | A1* | 12/2005 | Tanaka | A61B 1/00073 600/114 |
| 2008/0009675 | A1* | 1/2008 | Kura | A61B 1/00147 600/137 |
| 2009/0171152 | A1 | 7/2009 | Aoki et al. | |
| 2009/0209812 | A1 | 8/2009 | Omoto | |
| 2013/0035552 | A1 | 2/2013 | Moriyama | |
| 2014/0187865 | A1* | 7/2014 | Ishizaki | G02B 23/24 600/149 |

FOREIGN PATENT DOCUMENTS

| | | |
|---|---|---|
| JP | 2006-042900 A | 2/2006 |
| JP | 2006-230620 A | 9/2006 |
| JP | 2007-319547 A | 12/2007 |
| JP | 2008-093029 A | 4/2008 |
| WO | 2012/137365 A | 10/2012 |

OTHER PUBLICATIONS

English translation of International Preliminary Report on Patentability together with the Written Opinion dated Jan. 22, 2015 received in related International Application No. PCT/JP2013/068188.

International Search Report dated Oct. 1, 2013 issued in PCT/JP2013/068188.

Extended Supplementary European Search Report dated Apr. 19, 2016 in related European Application No. 13 81 7045.1.

\* cited by examiner

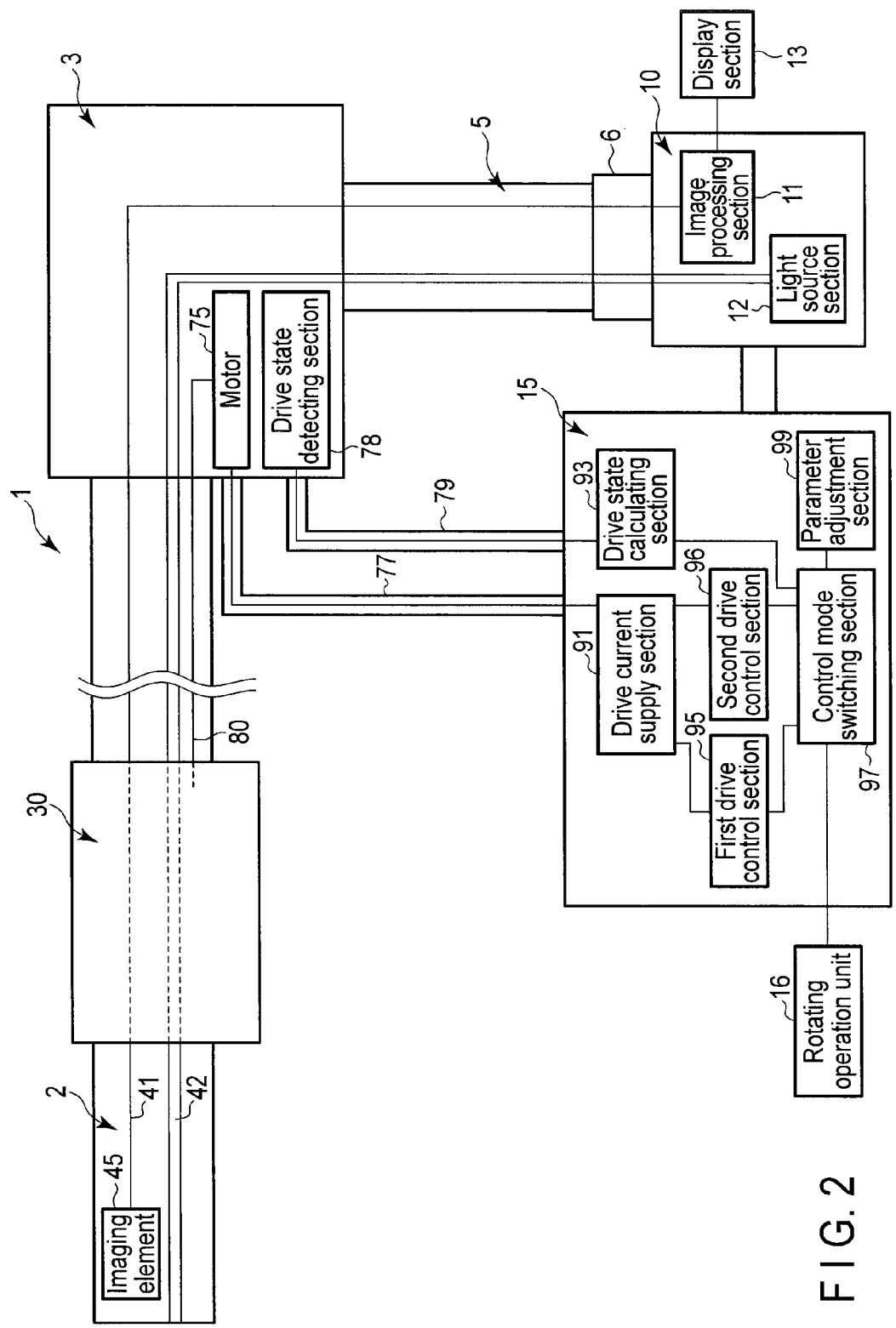
F I G. 2

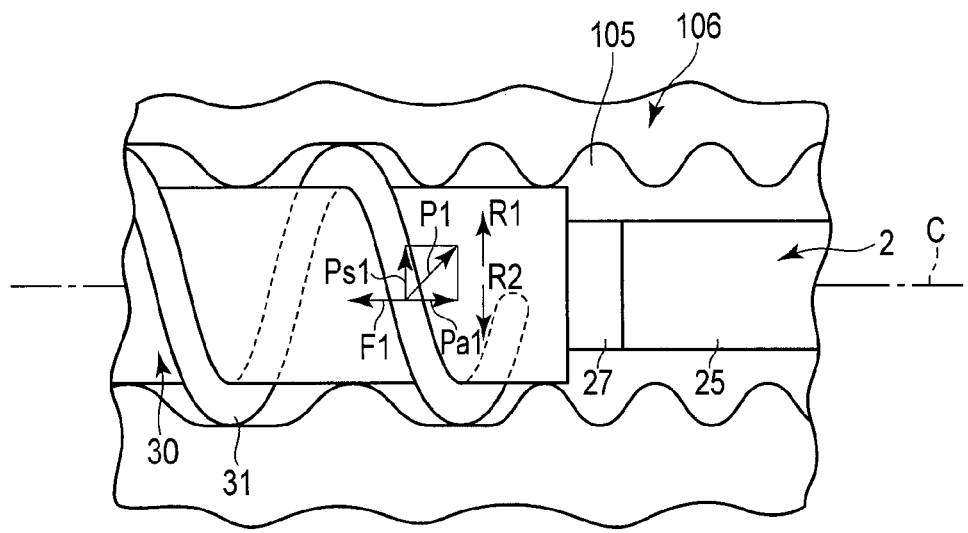
F I G. 5
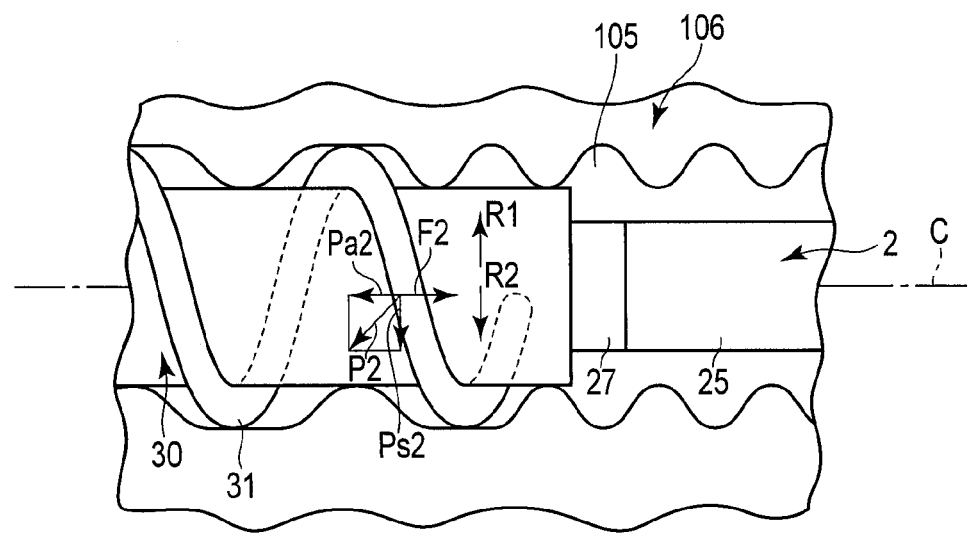
F I G. 6

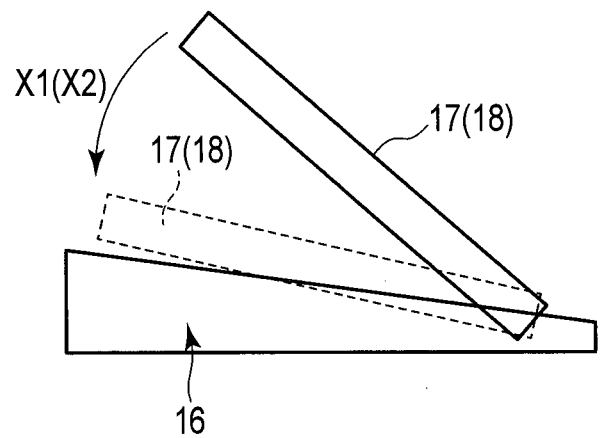
F I G. 7
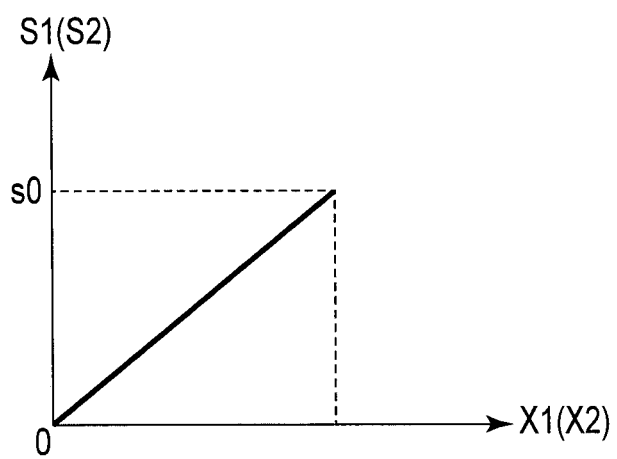
F I G. 8

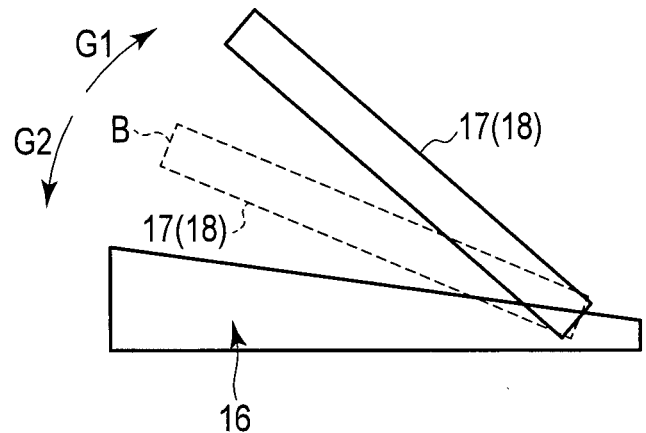
F I G. 15A
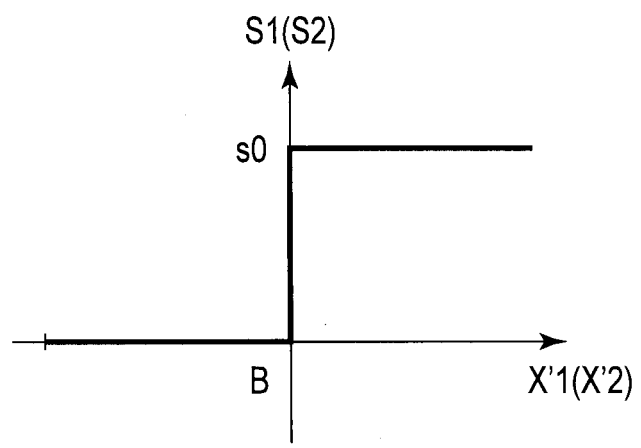
F I G. 15B

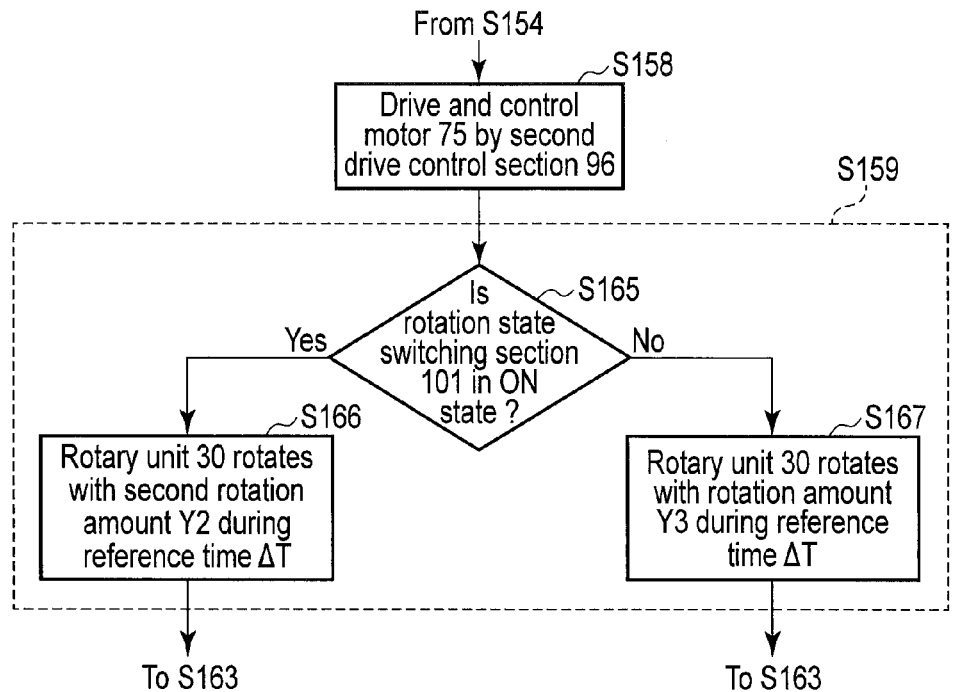
F I G. 17
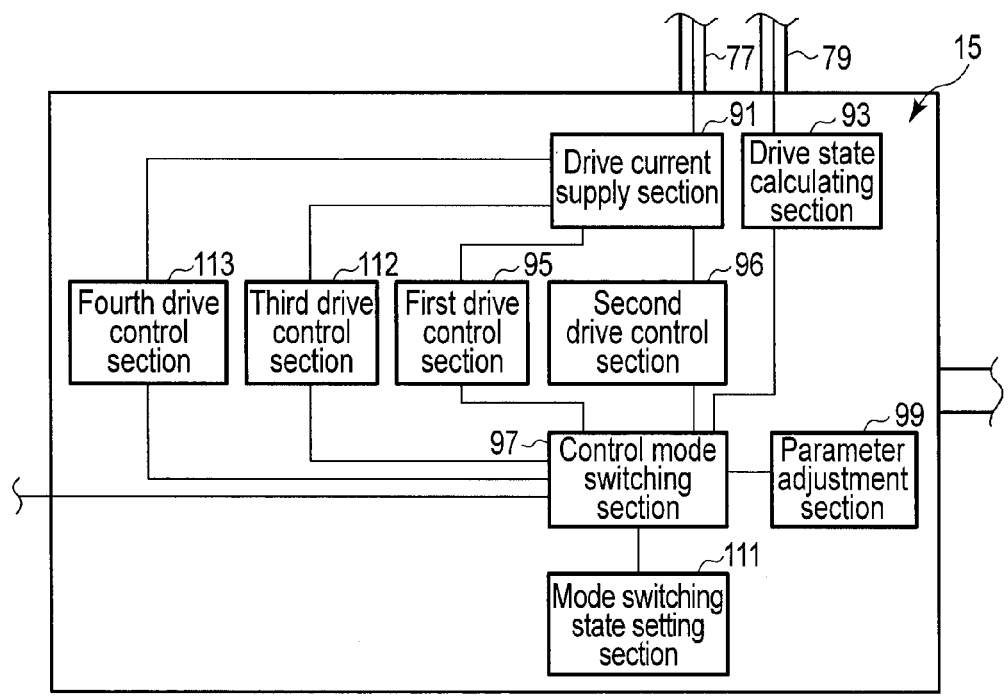
F I G. 18

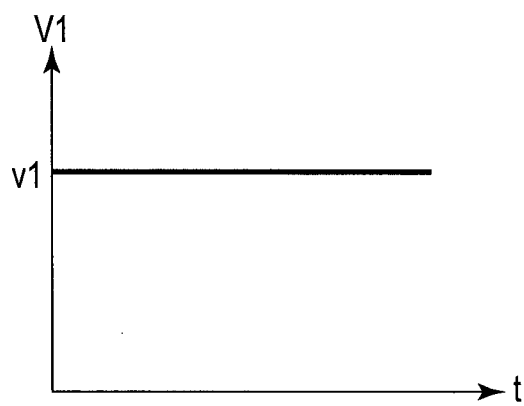
F I G. 19
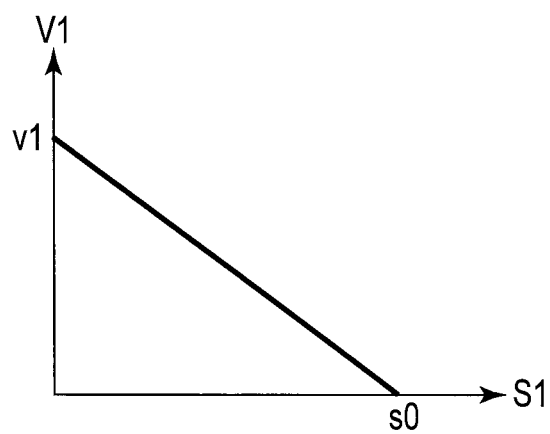
F I G. 20

INSERTION APPARATUS

CROSS-REFERENCE TO RELATED APPLICATIONS

This is a Continuation Application of PCT Application No. PCT/JP2013/068188, filed Jul. 2, 2013 and based upon and claiming the benefit of priority from prior Japanese Patent Application No. 2012-154629, filed Jul. 10, 2012, the entire contents of which are incorporated herein by reference.

BACKGROUND OF THE INVENTION

1. Field of the Invention

The present invention relates to an insertion apparatus including an inserting section extended along a longitudinal axis, and a rotary unit which is rotatable in directions around the longitudinal axis with respect to the inserting section.

2. Description of the Related Art

Jpn. Pat. Appln. KOKAI Publication No. 2008-93029 discloses an endoscope apparatus which is an insertion apparatus including an inserting section extended along a longitudinal axis, and a rotary unit which is rotatable in directions around the longitudinal axis with respect to the inserting section. The rotary unit includes a spiral fin portion spirally extended around the longitudinal axis. The spiral fin portion is placed toward a first periaxial direction side which is one of directions around the longitudinal axis as the spiral fin portion extends from a proximal direction toward a distal direction. In a lumen, when the rotary unit is rotated in the first periaxial direction in a state that the spiral fin portion is in contact with a luminal paries, a first propulsive force toward the distal direction acts on the inserting section and the rotary unit. On the other hand, when the rotary unit is rotated toward a second periaxial direction opposite to the first periaxial direction in the state that the spiral fin portion is in contact with the luminal paries, a second propulsive force toward the proximal direction acts on the inserting section and the rotary unit. Mobility of the inserting section in directions parallel to the longitudinal axis in the lumen can be improved by the first propulsive force and the second propulsive force.

Further, in this endoscope apparatus, a speed change operation button configured to input a speed change operation for changing a level of a rotating speed of the rotary unit is provided. With the speed change operation, a drive state of a motor as a drive member configured to generate a drive force of rotating the rotary unit is changed. When the speed change operation button is pressed, a magnitude of the rotating speed of the rotary unit is reduced by half as compared with a case where the speed change operation button is not pressed. Therefore, when the speed change operation button is pressed, rotation amounts of the rotary unit in the first periaxial direction and the second periaxial direction are reduced during a reference time having a predetermined length. When a magnitude of a first rotation amount of the rotary unit in the first periaxial direction during the reference time varies, an acting state of the first propulsive force changes, and a first moving amount of the inserting section toward the distal direction during the reference time changes. That is, when the first rotation amount of the rotary unit toward the first periaxial direction during the reference time is reduced, the first moving amount of the inserting section in the distal direction during the reference time is decreased. Likewise, when a magnitude of the second rotation amount of the rotary unit in the second periaxial direction during the reference time varies, an acting state of the second propulsive force changes, and a second moving amount of the inserting section toward the proximal direction during the reference time changes. That is, when the second rotation amount of the rotary unit toward the second periaxial direction during the reference time is reduced, the second moving amount of the inserting section in the proximal end direction during the reference time is decreased.

BRIEF SUMMARY OF THE INVENTION

According to one aspect of the invention, an insertion apparatus includes that: an inserting section which is extended from a proximal direction toward a distal direction along a longitudinal axis; a rotary unit which includes a spiral fin portion spirally extended around the longitudinal axis, and which is provided to an outer peripheral direction side of the inserting section in a state that the rotary unit is rotatable toward a first periaxial direction around the longitudinal axis and a second periaxial direction opposite to the first periaxial direction with respect to the inserting section; a drive member which is configured to generate a drive force of rotating the rotary unit; a rotating operation unit which is configured to input a first rotating operation of rotating the rotary unit toward the first periaxial direction and a second rotating operation of rotating the rotary unit toward the second periaxial direction; a first drive control section which is configured to drive and control a drive state of the drive member in such a manner that the rotary unit rotates toward the first periaxial direction with a first rotation amount during a reference time having a predetermined length or configured to adjust at least one of a current value and a voltage value of drive electric power in such a manner that a current having the first current amount is supplied to the drive member during the reference time, based on a first operation command generated by input of the first rotating operation; and a second drive control section which is configured to drive and control the drive state of the drive member in such a manner that the rotary unit rotates toward the second periaxial direction with a second rotation amount smaller than the first rotation amount during the reference time or configured to adjust at least one of the current value and the voltage value of the drive electric power in such a manner that the current having a second current amount smaller than the first current amount is supplied to the drive member during the reference time, based on a second operation command generated by input of the second rotating operation.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a block diagram schematically showing the endoscope apparatus according to the first embodiment;

FIG. 5 is a schematic view showing a state in which a rotary unit rotates toward a first periaxial direction in a lumen according to the first embodiment;

FIG. 6 is a schematic view showing a state in which the rotary unit rotates toward a second periaxial direction in the lumen according to the first embodiment;

FIG. 7 is a schematic view for explaining input of a first rotating operation in a first operation input section in a rotating operation unit according to the first embodiment;

FIG. 8 is a schematic view showing a relationship between a movement displacement of the first operation input section from a first input OFF position and a first command value of a first operation command in the rotating operation unit according to the first embodiment;

FIG. 15A is a schematic view for explaining input of the first rotating operation in the first operation input section of the rotating operation unit according to a third modification;

FIG. 15B is a schematic view showing a relationship between a movement displacement of the first operation input section from a boundary position and a first command value of a first operation command in the rotating operation unit according to the third modification;

FIG. 17 is a flowchart showing a method of rotating a rotary unit toward a second periaxial direction in a second control mode by a second drive control section according to the second embodiment;

FIG. 18 is a block diagram schematically showing a configuration of a control unit of an endoscope apparatus according to a third embodiment;

FIG. 19 is a schematic view showing a change with time of a first rotating speed of a rotary unit toward a first periaxial direction in rotation of the rotary unit in a third control mode according to the third embodiment; and FIG. 20 is a schematic view showing a relationship between a first command value of a first operation command and a magnitude of the first rotating speed of the rotary unit toward the first periaxial direction in rotation of the rotary unit in a fourth control mode according to the third embodiment.

DETAILED DESCRIPTION OF THE INVENTION

First Embodiment

Figure 1:
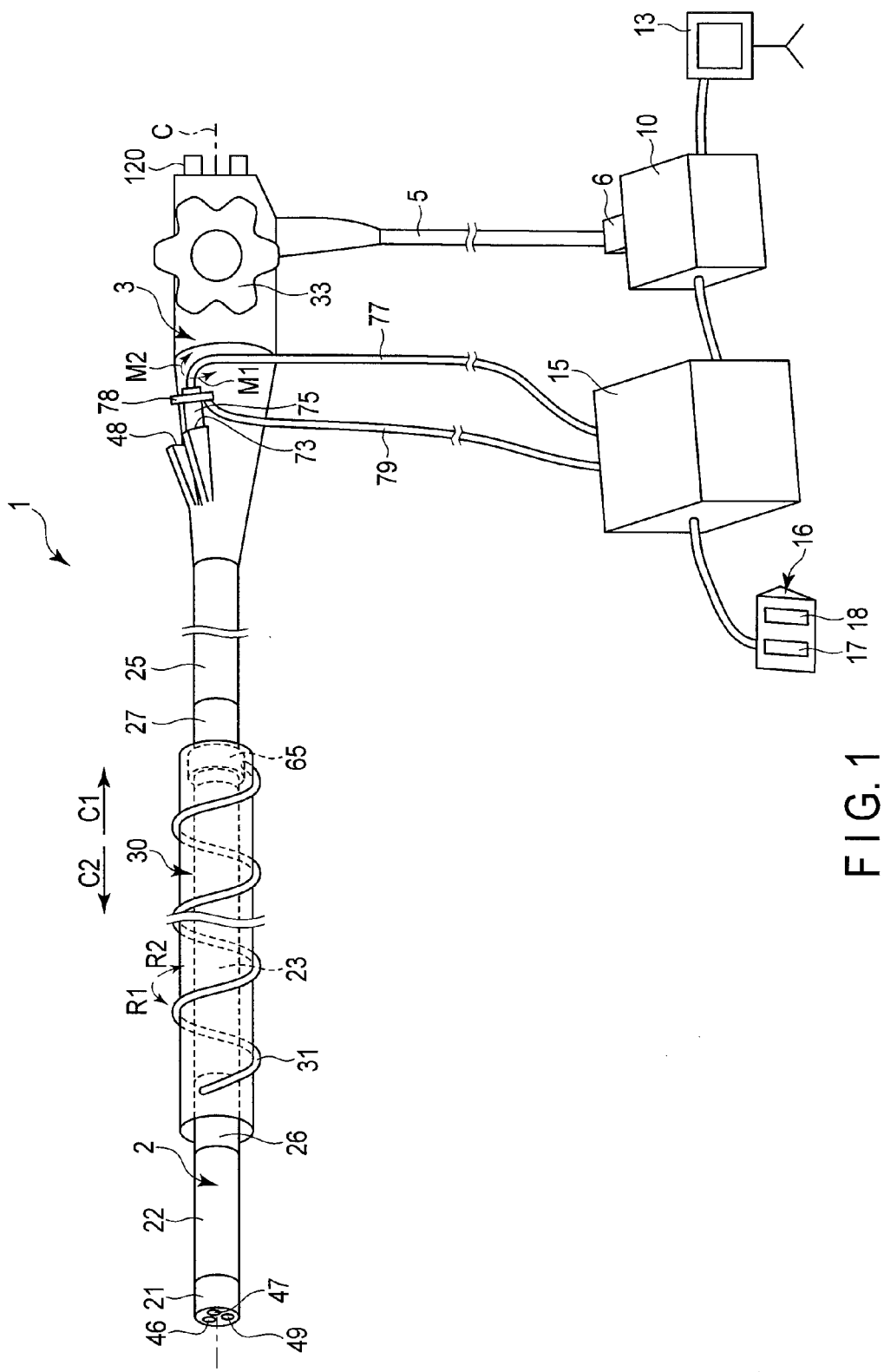
FIG. 1 is a schematic view showing an endoscope apparatus according to a first embodiment.

A first embodiment according to the present invention will now be described with reference to FIG. 1 to FIG. 11. FIG. 1 and FIG. 2 are views showing an endoscope apparatus 1 that is an insertion apparatus according to the first embodiment. As shown in FIG. 1, the endoscope apparatus 1 has a longitudinal axis C. One of directions parallel to the longitudinal axis C is a distal direction (a direction of an arrow C1 in FIG. 1), and a direction opposite to the distal direction is a proximal direction (a direction of an arrow C2 in FIG. 1). As shown in FIG. 1 and FIG. 2, the endoscope apparatus 1 includes an inserting section (an endoscope inserting section) 2 extended from the proximal direction toward the distal direction along the longitudinal axis C, and an operating section (an endoscope operating section) 3 provided to the proximal direction side with respect to the inserting section 2. The inserting section 2 is configured to be inserted into a lumen when the endoscope device 1 is used.

One end of a universal cable 5 is connected to the operating section 3. The other end of the universal cable 5 is connected to an observation processing unit 10 through a connector 6. The observation processing unit 10 includes an image processing section 11 and a light source section 12. The observation processing unit 10 is electrically connected to a display section 13 such as a monitor. Furthermore, the observation processing unit 10 is electrically connected to a control unit 15. The control unit 15 is electrically connected to a rotating operation unit 16 such as a foot switch. The rotating operation unit 16 includes a first operation input section 17 and a second operation input section 18.

The inserting section 2 includes a distal end hard section 21 provided most distally, a bending section 22 provided to the proximal direction side with respect to the distal end hard section 21, a first flexible section 23 provided to the proximal direction side with respect to the bending section 22, and a second flexible section 25 provided to the proximal direction side with respect to the first flexible section 23. The bending section 22 is connected to the first flexible tube section 23 through a first intermediary connecting section 26. Furthermore, the first flexible tube section 23 is connected to the second flexible tube section 25 through a second intermediary connecting section 27.

A rotary unit 30 is provided on an outer peripheral direction side of the insertion unit 2. The inserting section 2 is inserted in the rotary unit 30. The rotary unit 30 is extended between the first intermediary connecting section 26 and the second intermediary connecting section 27 along the longitudinal axis C. Moreover, the rotary unit 30 is rotatable in directions around the longitudinal axis with respect to the inserting section 2. Here, one of the directions around the longitudinal axis is a first periaxial direction (a direction of an arrow R1 in FIG. 1), and a direction opposite to the first periaxial direction is a second periaxial direction (a direction of an arrow R2 in FIG. 1). In this embodiment, a clockwise direction seen from the proximal direction side is the first periaxial direction, and a counterclockwise direction seen from the proximal direction side is the second periaxial direction. The rotary unit 30 includes a spiral fin portion 31 spirally extended around the longitudinal axis C. The spiral fin portion 31 is placed toward the first periaxial direction side as the spiral fin portion extends from the proximal direction toward the distal direction.

Figure 3:
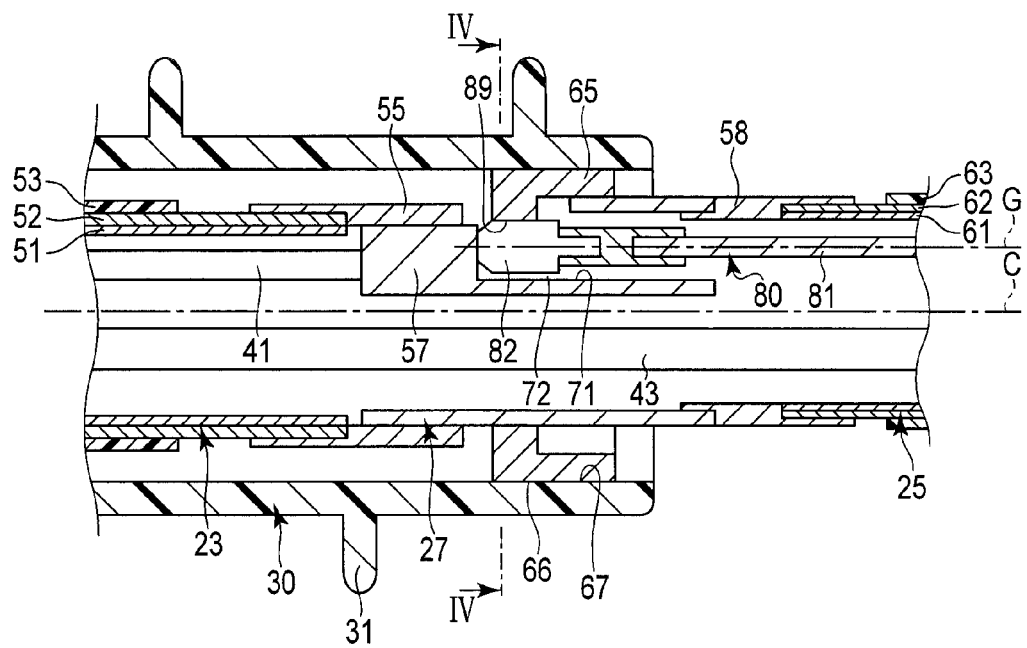
FIG. 3 is a cross-sectional view schematically showing a configuration of a second intermediary connecting section of the inserting section according to the first embodiment.
Figure 4:
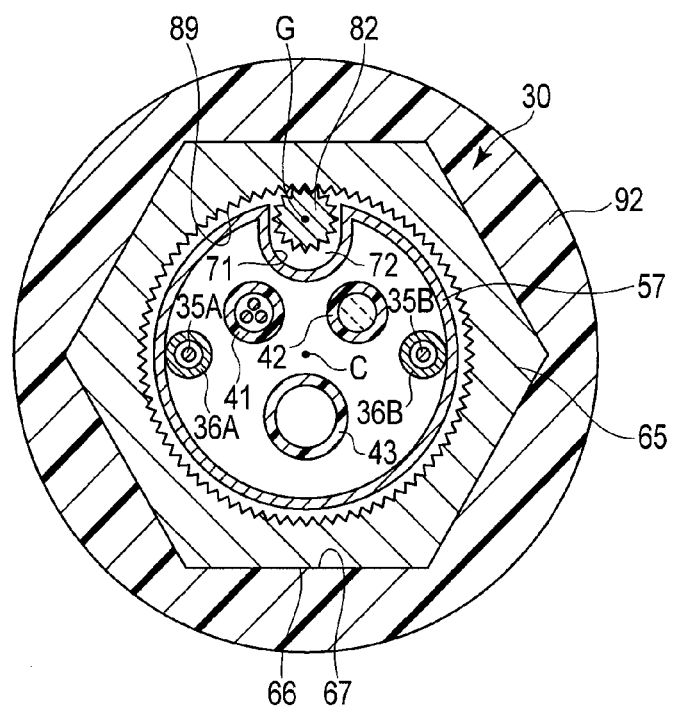
FIG. 4 is a cross-sectional view taken along a line IV-IV in FIG. 3.

FIG. 3 is a view showing a configuration of the second intermediary connecting section 27, and FIG. 4 is a cross-sectional view taken along a line IV-IV in FIG. 3. A bending operation knob 33 which is a bending operation input section by which a bending operation of the bending section 22 is input is provided on an outer surface of the operating section 3 as shown in FIG. 1. As shown in FIG. 4, bending wires 35A and 35B are extended inside the inserting section 2 along the longitudinal axis C. Inside the operating section 3, proximal ends of the bending wires 35A and 35B are connected to a pulley (not shown) coupled with the bending operation knob 33. Distal ends of the bending wires 35A and 35B are connected to a distal portion of the bending section 22. The bending wire 35A or the bending wire 35B is pulled by a bending operation of the bending operation knob 33, and the bending section 22 bends.

Each of the bending wires 35A and 35B is inserted through a corresponding coil 36A or 36B. Proximal ends of the coils 36A and 36B are fixed to an inner peripheral portion of the operating section 3. Further, distal ends of the coils 36A and 36B are connected to inner peripheral portion of the first intermediary connecting section 26. It is to be noted that, in this embodiment, the two bending wires 35A and 35B are provided, and the bending section 22 can bend in two directions but, for example, four bending wires may be provided so that the bending section 2 can bend in four directions. Moreover, the bending section 22 may not be provided.

As shown in FIG. 3 and FIG. 4, in the inserting section 2, an imaging cable 41, a light guide 42, and a treatment tool channel tube 43 are extended along the longitudinal axis C. An imaging element 45 configured to image a subject is provided in the distal hard section 21 (a distal portion of the inserting section 2) (see FIG. 2). The imaging element 45 is configured to image a subject through an observation window 46. A distal end of the imaging cable 41 is connected to the imaging element 45. The imaging cable 41 is extended through an inside of the inserting section 2, an inside of the operating section 3, and an inside of the universal cable 5, and a proximal end of the imaging cable 41 is connected to the image processing section 11 of the observation processing unit 10. The image processing section 11 executes image processing of a subject acquired image, thereby generating an image of the subject. Additionally, the generated image of the subject is displayed on the display section 13.

Further, the light guide 42 is extended through the inside of the inserting section 2, the inside of the operating section 3, and the inside of the universal cable 5, and a proximal end of the light guide 42 is connected to the light source section 12 of the observation processing unit 10. Light emitted from the light source section 12 is guided by the light guide 42 and applied to the subject from an illumination window 47 at the distal portion (the distal hard section 21) of the inserting section 2.

As shown in FIG. 1, a treatment tool inserting portion 48 into which a treatment tool such as forceps is inserted is provided on an outer surface of the operating section 3. A proximal end of the treatment tool channel tube 43 is connected to the treatment tool inserting portion 48 through the inside of the inserting section 2 and the inside of the operating section 3. The treatment tool inserted from the treatment tool inserting portion 48 protrudes toward the distal direction from an opening portion 49 of the distal hard section 21 through the treatment tool channel tube 43. Furthermore, in a state that the treatment tool protrudes from the opening portion 49 of the distal hard section 21, a treatment using the treatment tool is carried out.

As shown in FIG. 3, a first helical tube (a first flex) 51 made of a metal is provided to the first flexible tube section 23. An outer peripheral direction side of the first spiral tube 51 is covered with a first flexible reticular tube (a first flexible blade) 52 made of a metal. The outer peripheral direction side of the first flexible reticular tube 52 is covered with a first flexible envelope 53 made of a resin. A proximal portion of the first helical tube 51 and a proximal portion of the first flexible reticular tube 52 are fitted in a distal portion of an intermediary member 55. A second intermediary connecting section 27 includes a base member 57 made of a metal. A proximal portion of the intermediary member 55 is fitted on the base member 57. As described above, the first flexible tube section 23 is coupled with the second intermediary connecting section 27.

A second helical tube (a second flex) 61 made of a metal is provided in the second flexible tube section 25. An outer peripheral direction side of the second helical tube 61 is covered with a second flexible reticular tube (a second flexible blade) 62 made of a metal. An outer peripheral direction side of the second flexible reticular tube 62 is covered with a second flexible envelope 62 made of a resin. A distal portion of the second helical tube 61 and a distal portion of the second flexible reticular tube 62 are fitted in the intermediary member 58. The intermediary member 58 is fitted in the base member 57. As described above, the second flexible tube section 25 is coupled with the second intermediary connecting section 27.

In a state that the inserting section 2 is inserted through a rotating cylindrical member 65, the rotating cylindrical member 65 is attached to the second intermediary connecting section 27 of the inserting section 2. The rotating cylindrical member 65 is rotatable in directions around the longitudinal axis with respect to the inserting section 2. The rotary unit 30 is placed to an outer peripheral direction side of the rotating cylindrical member 65.

As shown in FIG. 4, a polygon-shaped outer peripheral portion 66 whose cross-sectional shape in a section perpendicular to the longitudinal axis C is a substantially hexagonal shape is provided on the rotating cylindrical member 65. Moreover, a polygon-shaped inner peripheral portion 67 is provided to the rotary unit 30, the polygon-shaped inner peripheral portion 67 being formed into a substantially hexagonal shape corresponding to the polygon-shaped outer peripheral portion 66 of the rotating cylindrical member 65 in the section perpendicular to the longitudinal axis C running through the rotating cylindrical member 65. Therefore, the polygon-shaped inner peripheral portion 67 of the rotary unit 30 is closely in contact with the polygon-shaped outer peripheral section 66 of the rotating cylindrical member 65, and the rotary unit 30 is fixed on the outer peripheral direction side of the rotating cylindrical member 65. As a result, the rotary unit 30 can rotate together with the rotating cylindrical member 65 in the directions around the longitudinal axis with respect to the inserting section 2. That is, the base member 57 is a base section to which the rotary unit 30 is attached through the rotating cylindrical member 65 in a state that the rotary unit 30 is rotatable in the directions around the longitudinal axis.

As shown in FIG. 2 and FIG. 3, in the base member 57 (a base section), a gear arrangement cavity 72 is defined by a cavity defining portion 71. The outside of the inserting section 2 communicates with the inside of the same through the gear arrangement cavity 72.

As shown in FIG. 1, a member inserting portion 73 is provided on an outer surface of the operating section 3. Further, a motor 75 as a drive member is attached to the member inserting portion 73. One end of a motor cable 77 is connected to the motor 75. The control unit 15 includes a drive current supply section 91. The other end of the motor cable 77 is connected to the drive current supply section 91. A drive current is supplied to the motor 75 by the drive current supply section 91 through the motor cable 77. The motor 75 can be driven to rotate toward directions, i.e., a first drive direction (a direction of an arrow M1 in FIG. 1) and a second drive direction (a direction of an arrow M2 in FIG. 1). When the motor 75 is driven, a drive force of rotating the rotary unit 30 in one of the directions around the longitudinal axis is generated.

Furthermore, a drive state detecting section 78 such as an encoder is disposed to the motor 75. A drive state of the motor 75 is detected by the drive state detecting section 78. One end of a signal cable 79 is connected to the drive state detecting section 78. Moreover, the control unit 15 includes a drive state calculating section 93. The other end of the signal cable 79 is connected to the drive state calculating section 93. The drive state calculating section 93 is configured to calculate a drive amount and a drive direction (a drive state) of the motor 75 based on a detection result obtained by the drive state detecting section 78.

The drive force generated by the motor 75 is transmitted to the rotary unit 30 by a drive force transmitting unit 80. As shown in FIG. 3 and FIG. 4, the drive force transmitting unit 80 is provided to the second flexible tube section 25 of the inserting section 2 and the gear arrangement cavity 72. The drive force transfer unit 80 is rotatable around a drive axis G. The drive force transmitting unit 80 includes a drive shaft 81 which is a linear member extended along the drive axis G, and a drive gear 82 provided to the distal direction side with respect to the drive shaft 81. The drive shaft 81 is coupled with the drive gear 82 through a connection member 85. Moreover, a proximal end of the drive shaft 81 is connected to the motor 75. When the motor 75 is driven, the drive shaft 81 and the drive gear 82 rotate in one of directions around the drive axis.

An inner peripheral gear portion 89 that meshes with the drive gear 82 is provided on an inner peripheral portion of the rotating cylindrical member 65. The inner peripheral gear portion 89 is provided on the entire periphery of the rotating cylindrical member 65 in the directions around the longitudinal axis. Therefore, when the drive gear 82 rotates around the drive axis G, the rotating cylindrical member 65 rotates in one of the directions around the longitudinal axis. When the rotating cylindrical member 65 rotates, the rotary unit 30 rotates in one of the directions around the longitudinal axis with respect to the inserting section 2. As described above, when the motor 75 is driven, the drive force for rotating the rotating cylindrical member 65 and the rotary unit 30 is transferred by the drive force transmitting unit 80. Here, when the motor 75 is driven to rotate in the first drive direction (the direction of the arrow M1 in FIG. 1), the rotary unit 30 rotates toward the first periaxial direction (the direction of the arrow R1 in FIG. 1) with respect to the inserting section 2. On the other hand, when the motor 75 is driven to rotate in the second drive direction (the direction of the arrow R2 in FIG. 1), the rotary unit 30 rotates toward the second periaxial direction (the direction of the arrow R2 in FIG. 1) with respect to the inserting section 2.

As shown in FIG. 2, the control unit 15 includes a first drive control section 95 and a second drive control section 96. The first drive control section 95 and the second drive control section 96 are electrically connected to the drive current supply section 91. In a state that the motor 75 is driven to rotate toward the first drive direction, a current supplied from the drive current supply section 91 is adjusted by the first drive control section 95, and a rotating state (a drive state) of the motor 75 is controlled. On the other hand, in a state that the motor 75 is driven to rotate toward the second drive direction, a current supplied from the drive current supply section 91 is adjusted by the second drive control section 96, and a rotating state (a drive state) of the motor 75 is controlled.

Additionally, the control unit 15 includes a control mode switching section 97. The control mode switching section 97 is electrically connected to the first drive control section 95 and the second drive control section 96. Further, the control mode switching section 97 is electrically connected to the rotating operation unit 16. In the first operation input section 17 of the rotating operation unit 16, a first rotating operation for rotating the rotary unit 30 toward the first around-axis direction can be input. When the first rotating operation is input, a first operation command is generated. When the generated first operation command is transmitted, the control mode switching section 97 switches to a first control mode in which the first drive control section 95 executes drive control over the motor 75. Furthermore, in the second operation input section 18 of the rotating operation unit 16, a second rotating operation for rotating the rotary unit 30 toward the second around-axis direction can be input. When the second rotating operation is input, a second operation command is generated. When the generated second operation command is transmitted, the control mode switching section 97 switches to a second control mode in which the second drive control section 96 executes drive control over the motor 75.

The control mode switching section 97 is electrically connected to the drive state calculating section 93. A calculated drive state of the motor 75 is fed back to the first drive control section 95 in the first control mode, and is fed back to the second drive control section 96 in the second control mode. Additionally, the control unit 15 includes a parameter adjustment section 99. The parameter adjustment section 99 is electrically connected to the first drive control section 95 and the second drive control section 96.

Functions and effects of the endoscope apparatus 1 according to this embodiment will now be described. When the endoscope device 1 is used, the inserting section 2 having the rotating cylindrical member 65 and the rotary unit 30 attached thereto is inserted into a lumen. Further, the motor 75 is driven by an operation in the rotating operation unit 16. As a result, the drive force transmitting unit 80' rotates around the drive axis G, and the drive force is transmitted to the rotating cylindrical member 65 and the rotary unit 30. As a result, the rotating cylindrical member 65 and the rotary unit 30 integrally rotate in one of the directions around the longitudinal axis with respect to the inserting section 2.

FIG. 5 is a view for explaining a state in which the rotary unit 30 rotates toward the first periaxial direction (a direction of an arrow R1 in FIG. 5) in a lumen 105 such as a small intestine or a large intestine. As shown in FIG. 5, in the lumen 105, the spiral fin portion 31 on the rotary unit 30 is in contact with a lumen paries 106. Therefore, the rotary unit 30 is in a pressing state in which a pressing force acts on the spiral fin portion 31 from the lumen paries toward the inner peripheral direction. In the pressing state, when the rotary unit 30 is rotated toward the first periaxial direction, pressing force P1 acts on the lumen paries 106 from the spiral fin portion 31. The pressing force P1 acts toward a direction which is inclined with respect to the first around-axis direction toward the proximal direction and which is perpendicular to an extending direction of the spiral fin portion 31. The pressing force P1 is divided into a circumferential force component Ps1 toward the first periaxial direction and an axial force component Pa1 toward the proximal direction. As a reaction of the axial force component Pa1 of the pressing force P1, first propulsive force F1 in the distal direction acts on the inserting section 2 and the rotary unit 30 from the lumen paries 106. The first propulsive force F1 improves insertability of the inserting section 2 in the lumen 105. That is, in the lumen 105, mobility of the inserting section 2 toward the distal direction parallel to the longitudinal axis C is improved.

FIG. 6 is a view for explaining a state in which the rotary unit 30 rotates toward the second periaxial direction (a direction of an arrow R2 in FIG. 6) in the lumen 105. As shown in FIG. 6, when the rotary unit 30 is rotated toward the second periaxial direction in the pressing state, pressing force P2 acts on the lumen paries 106 from the spiral fin portion 31. The pressing force P2 acts toward a direction which is inclined with respect to the second around-axis direction toward the distal direction and which is perpendicular to the extending direction of the spiral fin portion 31. The pressing force P2 is divided into a circumferential force component Ps2 toward the second periaxial direction and an axial force component Pa2 toward the distal direction. As a reaction of the axial force component Pa2 of the pressing force P2, second propulsive force F2 in the proximal direction acts on the inserting section 2 and the rotary unit 30 from the lumen paries 106. The second propulsive force F2 improves removability of the inserting section 2 from the lumen 105. That is, in the lumen 105, mobility of the inserting section 2 toward the proximal direction parallel to the longitudinal axis C is improved.

FIG. 7 is a view for explaining input of the first rotating operation in the first operation input section 17 of the rotating operation unit 16. As shown in FIG. 7, the first operation input section 17 can move between a first input OFF position (a position indicated by a solid line in FIG. 7) and a first maximum input position (a position indicated by a dotted line in FIG. 7). The first operation command is not generated at the first input OFF position. Further, when the first operation input section 17 moves from the first input OFF position, the first rotating operation is input, and the first operation command is generated. FIG. 8 is a view showing a relationship between a movement displacement X1 of the first operation input section 17 from the first input OFF position and a first command value S1 which is a command value of the first operation command. As shown in FIG. 8, as the movement displacement X1 of the first operation input section 17 with the first input OFF position being a standard increases, the first command value S1 of the first operation command rises. Furthermore, at the first maximum input position, the first command value S1 of the first operation command becomes maximum. At the first maximum input position, the first command value S1 of the first operation command has a magnitude s0.

Input of the second rotating operation in the second operation input section 18 is the same as the input of the first rotating operation. That is, the second operation input section 18 can move between a second input OFF position and a second maximum input position. At the second input OFF position, the second operation command is not generated. Moreover, when the second operation input section 18 moves from the second input OFF position, the second rotating operation is input, and the second operation command is generated. As the movement displacement X2 of the second operation input section 18 from the second input OFF position increases, a second command value S2 which is a command value of the second operation command rises. Additionally, at the second maximum input position, the second command value S2 of the second operation command becomes maximum. At the second maximum input position, the second command value S2 of the second operation command has a magnitude s0 which is the same as the first command value S1 of the first operation command at the first maximum input position.

Figure 9:
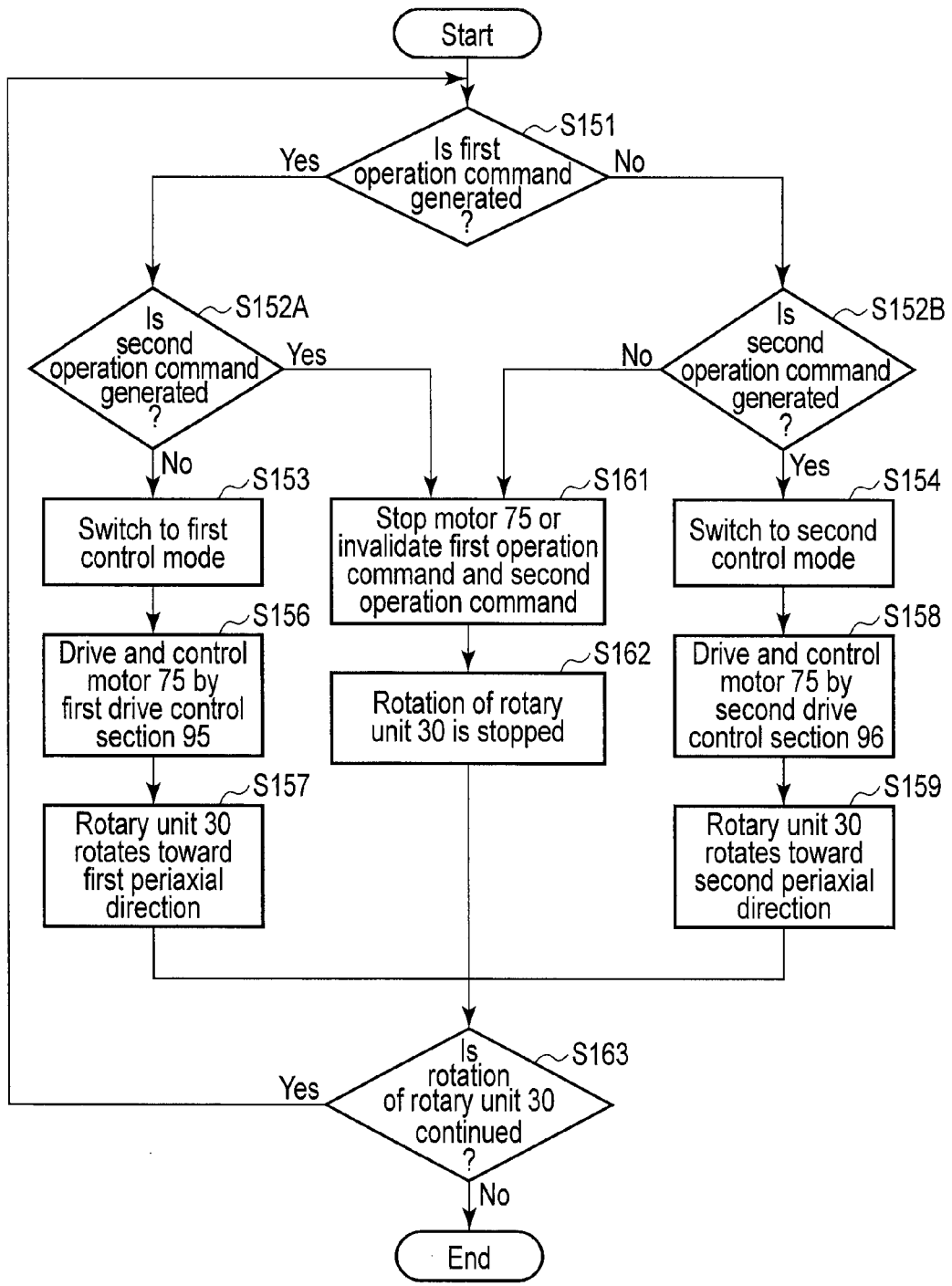
FIG. 9 is a flowchart showing a method of rotating the rotary unit by input of the first rotating operation or a second rotating operation in the rotating operation unit according to the first embodiment.

FIG. 9 is a view showing a method of rotating the rotary unit 30 by input of the first rotating operation or the second rotating operation. As shown in FIG. 9, in the case of driving the motor 75 and rotating the rotary unit 30 in one of the directions around the longitudinal axis, the control mode switching section 97 first determines whether the first operation command is generated (a step S151). Additionally, the control mode switching section 97 determines whether the second operation command is generated (steps S152A and S152B). If the first operation command is generated (the step S151—Yes) but the second operation command is not generated (the step S152A—No), a current mode is switched to the first control mode (a step S153). On the other hand, if the first operation command is not generated (the step S151—No) but the second operation command is generated (the step S152B—Yes), the current mode is switched to the second control mode (a step S154).

In the first control mode, the motor 75 is controlled to be driven by the first drive control section 95 (a step S156). As a result, the motor 75 is driven to rotate toward the first drive direction, and the rotary unit rotates toward the first periaxial direction (a step S157). On the other hand, in the second control mode, the motor 75 is controlled to be driven by the second drive control section 96 (a step S158). As a result, the motor 75 is driven to rotate toward the second drive direction, and the rotary unit 30 rotates toward the second periaxial direction (a step S159).

It is to be noted that, if the first operation command and the second operation command are generated (the step S151—Yes, the step S152A—Yes) and if the first operation command and the second operation command are not generated (the step S151—No, the step S152B—No), the motor 75 is stopped, or the first operation command and the second operation command are invalidated (a step S161). As a result, rotation of the rotary unit 30 is stopped (a step S162). Further, in the case of continuing the rotation of the rotary unit 30 (the step S163—Yes), the processing returns to the step S151, and the above-described steps are carried out over time.

Figure 10:
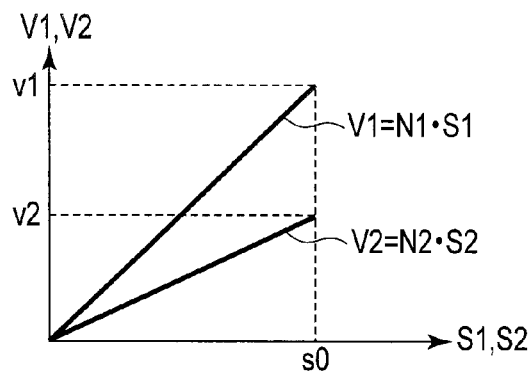
FIG. 10 is a schematic view showing a relationship between the first command value of the first operation command and a magnitude of the first rotating speed of the rotary unit toward the first periaxial direction and a relationship between a second command value of a second operation command and a magnitude of a second rotating speed of the rotary unit toward the second periaxial direction in rotation of the rotary unit according to the first embodiment.
Figure 11:
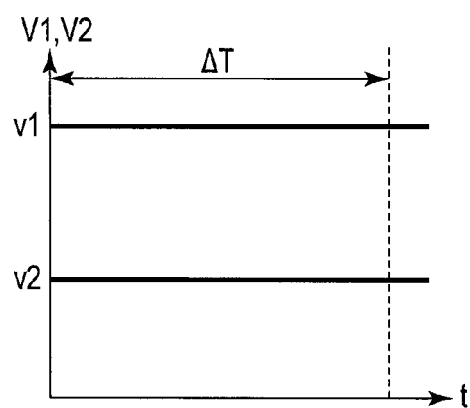
FIG. 11 is a schematic view showing change with time of the first rotating speed when the first operation input section is placed at a first maximum input position throughout the reference time and change with time of the second rotating speed when the second operation input section is placed at a second maximum input position throughout the reference time according to the first embodiment.

FIG. 10 is a view showing a relationship between the first command value S1 of the first operation command and a magnitude of a first rotating speed V1 of the rotary unit 30 toward the first periaxial direction and a relationship between the second command value S2 of the second operation command and a magnitude of a second rotating speed V2 of the rotary unit 30 toward the second periaxial direction. FIG. 11 shows change with time of the first rotating speed V1 when the first operation input section 17 is placed at the first maximum input position throughout a reference time $\Delta T$ having a predetermined time and change with time of the second rotating speed V2 when the second operation input section 18 is placed at the second maximum input position throughout the reference time $\Delta T$. That is, it is a view showing changes with time of a magnitude of the first rotating speed V1 when the first command value S1 has a magnitude s0 that is fixed over time and a magnitude of the second rotating speed V2 when the second command value S2 has a magnitudes s0 that is fixed over time.

As shown in FIG. 10, in the first control mode, the first drive control section 95 drives and controls the motor 75 in such a manner that the first rotating speed V1 of the rotary unit 30 toward the first around-axis direction increases as the first command value S1 of the first operation command rises. Further, the first rotating speed V1 is proportionate to the first command value S1 at a first ratio N1. Furthermore, in the second control mode, the second drive control section 96 drives and controls the motor 75 in such a manner that the second rotating speed V2 of the rotary unit 30 toward the second around-axis direction increases as the second command value S2 of the second operation command rises. Moreover, the second rotating speed V2 is proportionate to the second command value S2 at a second ratio N2. The second ratio N2 is smaller than the first ratio N1.

As shown in FIG. 11, assuming that the first command value S1 in the first control mode has the magnitude s0 that is fixed over time, the first rotating speed V1 has a fixed magnitude v1 throughout the reference time $\Delta T$ having the predetermined length. Moreover, assuming that the second command value S2 in the second control mode has the magnitude s0 that is fixed over time, the second rotating speed V2 has a fixed magnitude v2 throughout the reference time $\Delta T$. As described above, the second ratio N2 is smaller than the first ratio N1. Therefore, the magnitude v2 of the second rotating speed V2 of the rotary unit 30 when the magnitude of the second command value S2 in the second control mode is s0 is smaller than the magnitude v1 of the first rotating speed V1 of the rotary unit 30 when the first command value S1 in the first control mode is s0. That is, when the first command value S1 during a period of the reference time $\Delta T$ in the first control mode and the second command value S2 during the period of the reference time $\Delta T$ in the second control mode have the same magnitude, the second rotating speed V2 of the rotary unit 30 in the second control mode is smaller than the first rotating speed V1 of the same in the first control mode.

Since the first rotating speed V1 of the rotary unit 30 toward the first periaxial direction is controlled as described above, the rotary unit 30 rotates with a first rotation amount Y1 toward the first periaxial direction during the reference time $\Delta T$ in the first control mode. Additionally, since the second rotating speed V2 of the rotary unit 30 toward the second periaxial direction is controlled as described above, the rotary unit 30 rotates with a second rotation amount Y2 toward the second periaxial direction during the reference time $\Delta T$ in the second control mode. When the first command value S1 during the reference time $\Delta T$ in the first control mode and the second command value S2 during the reference time $\Delta T$ in the second control mode have the same magnitude, the second rotating speed V2 of the rotary unit 30 is smaller than the first rotating speed V1 throughout the reference time $\Delta T$. Therefore, when the first command value S1 during the reference time $\Delta T$ in the first control mode and the second command value S2 during the reference time $\Delta T$ in the second control mode have the same magnitude, the second propulsive force F2 in the second control mode is smaller than the first propulsive force F1 in the first control mode, and the second rotation amount Y2 during the reference time $\Delta T$ in the second control mode is smaller than the first rotation amount Y1 during the reference time $\Delta T$ in the first control mode. For example, the second rotation amount Y2 of the rotary unit 30 when the second operation input section 18 is placed at the second maximum input position throughout the reference time $\Delta T$ is smaller than the first rotation amount Y1 of the rotary unit 30 when the first operation input section 17 is placed at the first maximum input position throughout the reference time $\Delta T$.

Therefore, in the endoscope apparatus 1, when the first command value S1 during the reference time $\Delta T$ in the control mode and the second command value S2 during the reference time $\Delta T$ in the second control mode are set to have the same magnitude, the second rotation amount Y2 of the rotary unit 30 toward the second periaxial direction during the reference time $\Delta T$ provided by the second rotating operation is smaller than the first rotation amount Y1 of the rotary unit 30 toward the first periaxial direction during the reference time $\Delta T$ provided by the first rotating operation. Therefore, to reduce the second rotation amount Y2 of the rotary unit 30 during the reference time $\Delta T$ in the second control mode to be smaller than the first rotation amount Y1 of the rotary unit 30 during the reference time $\Delta T$ in the first control mode, a speed change operating section (a speed change operation button) or the like that enables inputting a speed change operation for changing a magnitude of a rotating speed of the rotary unit 30 does not have to be provided separately from the rotating operation unit 16. That is, the second rotation amount Y2 of the rotary unit 30 during the reference time $\Delta T$ provided by the second rotating operation can be smaller than the first rotation amount Y1 of the rotary unit 30 during the reference time $\Delta T$ provided by the first rotating operation without performing a speed change operation or the like in addition to the first rotating operation or the second rotating operation.

The parameter adjustment section 99 can adjust the first ratio N1 of the first rotating speed V1 of the rotary unit 30 relative to the first command value S1 of the first operation command. Further, the parameter adjustment section 99 can adjust the second ratio N2 of the second rotating speed V2 of the rotary unit 30 relative to the second command value S2 of the second operation command as long as the second ratio N2 becoming smaller than the first ratio N1. The parameter adjustment section 99 may be, e.g., a dial or a button provided on the control unit 15, and it may be provided in a scope switch 120 in FIG. 1. When the parameter adjustment section 99 provided in the above-described region is operated, the first ratio N1 and the second ratio N2 are changed. As a result, an operator can change a magnitude of the first rotating speed V1 of the rotary unit 30 at the time of inserting the inserting section 2 and a magnitude of the second rotating speed V2 of the rotary unit 30 at the time of removing the inserting section 2.

The parameter adjustment section 99 provided on the control unit 15 or provided in the scope switch 120 in FIG. 1 may be formed of two dials or buttons. In this case, a magnitude of the first rotating speed V1 of the rotary unit 30 at the time of inserting the inserting section 2 is adjusted by one dial or button, and a magnitude of the second rotating speed V2 of the rotary unit 30 at the time of removing the inserting section 2 is adjusted by the other dial or button. When the first rotating speed V1 is adjusted by the dial or the button different from the dial or the button used to adjusting the second rotating speed V2, a minimum value of the magnitude of the first rotating speed V1 is larger than a maximum value of the magnitude of the second rotating speed V2.

It is to be noted that, in place of the magnitude of the first rotating speed V1, a voltage value or a current value of the motor 75 at the time of rotating the rotary unit 30 toward the first periaxial direction may be proportionate to the first command value S1. Likewise, in place of the magnitude of the second rotating speed V2, a voltage value or a current value of the motor 75 at the time of rotating the rotary unit 30 toward the second periaxial direction may be proportionate to the second command value S2. In this case, a first proportional constant of the voltage value or the current value relative to the first command value S1 and a second proportional constant of the voltage value or the current value relative to the second command value S2 can be adjusted by the parameter adjustment section 99.

In a case of observing the lumen 105, e.g., a small intestine or a large intestine by using the endoscope apparatus 1, the inserting section 2 is moved at a high speed toward the distal direction until it reaches a position located to the distal direction side with respect to an observation region in the lumen 105. Furthermore, the observation region is observed while moving the inserting section 2 toward the proximal direction at a low speed or intermittently. Therefore, in a case of observing the lumen 105, for example, a second moving speed U2 at which the inserting section 2 is moved toward the proximal direction while observing the observation region in the lumen 105 is adjusted to be smaller than a first moving speed U1 at which the inserting section 2 is moved from toward the distal direction until it reaches the part located to the distal direction side of the observation region in the lumen 105. In this case, a second movement amount D2 by which the inserting section 2 moves in the proximal direction in the lumen 105 during the reference time ΔT is smaller than a first movement amount D1 by which the inserting section 2 moves in the distal direction in the lumen 105 during the reference time ΔT having the predetermined length.

Here, the first movement amount D1 of the inserting section 2 toward the distal direction during the reference time ΔT varies in accordance with an acting state of the first propulsive force F1 and also varies in accordance with the first rotation amount Y1 of the rotary unit 30 toward the first periaxial direction during the reference time ΔT. That is, as the first rotation amount Y1 increases, the first movement amount D1 also rises. Moreover, the second movement amount D2 of the inserting section 2 toward the proximal direction during the reference time ΔT varies in accordance with an acting state of the second propulsive force F2 and also varies in accordance with the second rotation amount Y2 of the rotary unit 30 toward the second periaxial direction during the reference time ΔT. That is, as the second rotation amount Y2 increases, the second movement amount D2 rises.

As described above, in the endoscope apparatus 1, the second rotation amount Y2 of the rotary unit 30 during the reference time ΔT provided by the second rotating operation can be smaller than the first rotation amount Y1 of the rotary unit 30 during the reference time ΔT provided by the first rotating operation without performing a speed change operation or the like in addition to the first rotating operation or the second rotating operation. Therefore, in a case of moving the inserting section 2 toward the distal direction in the lumen 105 until it reaches a position located on the distal direction side of the observation region, the first rotating operation is input, and the first drive control section 95 drives and controls the motor 75 in the first control mode. As a result, the first rotation amount Y1 of the rotary unit 30 toward the first periaxial direction during the reference time ΔT increases, and the inserting section 2 and the rotary unit 30 move toward the distal direction at the first moving speed U1 which is a high speed in the lumen 105. When the inserting section 2 and the rotary unit 30 move at the high speed, the first movement amount D1 of the inserting section 2 in the distal direction during the reference time ΔT increases.

On the other hand, in a case of observing the observation region while moving the inserting section 2 toward the proximal direction in the lumen 105, the second rotating operation is input, and the second drive control section 96 drives and controls the motor 75 in the second control mode. As a result, the second rotation amount Y2 of the rotary unit 30 toward the second periaxial direction during the reference time ΔT becomes smaller than the first rotation amount Y1, and the inserting section 2 and the rotary unit 30 move toward the proximal direction at the second moving speed U2 which is a low speed in the lumen 105. When the inserting section 2 and the rotary unit 30 move at the low speed, the second movement amount D2 of the inserting section 2 in the proximal direction during the reference time ΔT becomes smaller than the first movement amount D1.

As described above, in the endoscope apparatus 1, the inserting section 2 can be moved toward the distal direction in the lumen 105 at the high speed until it reaches a position to the distal direction side with respect to the observation region by the first rotating operation, and the observation region can be observed while moving the inserting section 2 toward the proximal direction at the low speed by the second rotating operation, both above movements of insertion section 2 being able to be performed without performing a speed change operation or the like in addition to the first rotating operation or the second rotating operation. Therefore, when the second rotating operation alone is performed, the observation of the lumen 105 can be appropriately performed while moving the inserting section 2 toward the proximal direction. That is, the observation of the lumen 105 while moving the inserting section 2 toward the proximal direction can be appropriately performed by an easy operation.

Modifications of First Embodiment

Figure 12:
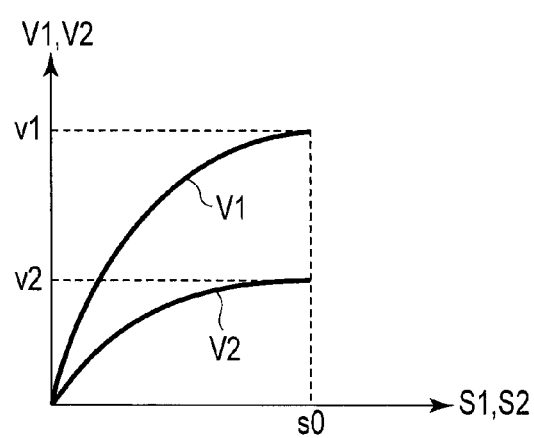
FIG. 12 is a schematic view showing a relationship between the first command value of the first operation command and the magnitude of the first rotating speed of the rotary unit toward the first periaxial direction and a relationship between the second command value of the second operation command and the magnitude of the second rotating speed of the rotary unit toward the second periaxial direction in rotation of the rotary unit according to a first modification.

It is to be noted that the first rotating speed V1 is proportionate to the first command value S1 at the first ratio N1 and the second rotating speed V2 is proportionate to the second command value S2 at the second ratio smaller than the first ratio N1 in the first embodiment, but the present invention is not restricted thereto. For example, as a first modification, the first rotating speed V1 may not be proportionate to the first command value S1 of the first operation command and the second rotation speed V2 may not be proportionate to the second command value S2 of the second operation command as shown in FIG. 12.

However, in this modification, like the first embodiment, in the first control mode, the first drive control section 95 drives and controls the motor 75 in such a manner that the first rotating speed V1 of the rotary unit 30 toward the first periaxial direction increases as the first command value S1 of the first operation command rises. Further, in the second control mode, the second drive control section 96 drives and controls the motor 75 in such a manner that the second rotating speed V2 of the rotary unit 30 toward the second periaxial direction increases as the second command value S2 of the second operation command rises. Moreover, if the first command value S1 during the reference time ΔT in the first control mode and the second command value S2 during the reference time ΔT in the second control mode have the same magnitude, the second rotating speed V2 of the rotary unit 30 throughout the reference time ΔT in the second control mode is smaller than the first rotating speed V1 throughout the reference time ΔT in the first control mode. Therefore, if the first command value S1 during the reference time ΔT in the first control mode and the second command value S2 during the reference time ΔT in the second control mode have the same magnitude, the second rotation amount Y2 of the rotary unit 30 during the reference time ΔT provided by the second rotating operation is smaller than the first rotation amount Y1 of the rotary unit 30 during the reference time ΔT provided by the first rotating operation. Therefore, the second rotation amount Y2 of the rotary unit 30 during the reference time ΔT provided by the second rotating operation can be smaller than the first rotation amount Y1 of the rotary unit 30 during the reference time ΔT provided by the first rotating operation without performing a speed change operation or the like in addition to the first rotating operation or the second rotating operation.

Figure 13:
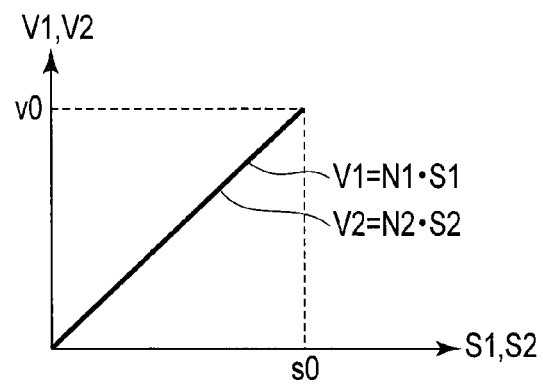
FIG. 13 is a schematic view showing a relationship between the first command value of the first operation command and the magnitude of the first rotating speed of the rotary unit toward the first periaxial direction and a relationship between the second command value of the second operation command and the magnitude of the second rotating speed of the rotary unit toward the second periaxial direction in rotation of the rotary unit according to a second modification.
Figure 14A:
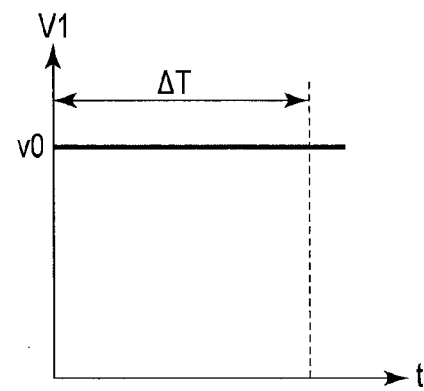
FIG. 14A is a schematic view showing a change with time of the first rotating speed when the first operation input section is placed at the first maximum input position throughout the reference time according to a second modification.
Figure 14B:
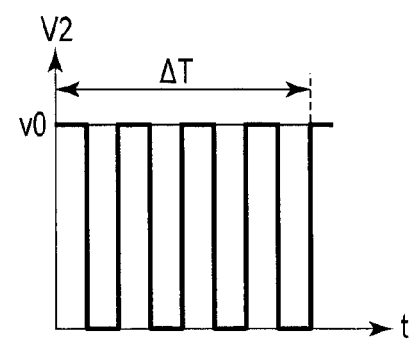
FIG. 14B is a schematic view showing a change with time of the second rotating speed when the second operation input section is placed at the second maximum input position throughout the reference time according to the second modification.

Additionally, in the first embodiment, if the first command value S1 during the reference time ΔT in the first control mode and the second command value S2 during the reference time ΔT in the second control mode have the same magnitude, the second rotating speed V2 of the rotary unit 30 during the reference time ΔT in the second control mode is smaller than the first rotating speed V1 during the reference time ΔT in the first control mode, but the present invention is not restricted thereto. For example, as a second modification, if the first command value S1 during the reference time ΔT in the first control mode and the second command value S2 during the reference time ΔT in the second control mode have the same magnitude, the first rotating speed V1 of the rotary unit 30 toward the first around-axis direction in the first control mode and the second rotating speed V2 of the rotary unit 30 toward the second around-axis direction in the second control mode may have the same magnitude as shown in FIG. 13 to FIG. 14B. Further, in this modification, the first ratio N1 of the first rotating speed V1 relative to the first command value S1 is equal to the second ratio N2 of the second rotating speed V2 relative to the second command S2.

FIG. 13 is a view showing a relationship between the first command value of the first operation command and a magnitude of the first rotating speed V1 of the rotary unit 30 toward the first periaxial direction and a relationship between the second command value S2 of the second operation command and a magnitude of the second rotating speed V2 of the rotary unit 30 toward the second periaxial direction. FIG. 14A shows a change with time of the first rotating speed V1 when the first operation input section 17 is placed at the first maximum input position throughout the reference time ΔT having the predetermined length, and FIG. 14B shows a change with time of the second rotating speed V2 when the second operation input section 18 is placed at the second maximum input position throughout the reference time ΔT. That is, FIG. 14A is a view showing a change with time of a magnitude of the first rotating speed V1 when the first command value S1 has a magnitude s0 that is fixed over time, and FIG. 14B is a view showing a change with time of a magnitude of the second rotating speed V2 when the second command value S2 has a magnitude s0 that is constant over time.

In this modification, when the first command value S1 during the reference time ΔT in the first control mode has the magnitude s0 that is fixed over time, the first rotating speed V1 in the first control mode has a fixed magnitude v0 throughout the reference time ΔT having the predetermined length. Further, when the second command value S2 during the reference time ΔT in the second control mode has the magnitude s0 that is fixed over time, the second rotating speed V2 in the second control mode has the magnitude v0 that is the same as the first rotating speed V1 during the reference time ΔT in the first control mode. However, in this modification, the rotary unit 30 intermittently rotates toward the second periaxial direction throughout the reference time ΔT in the second control mode. That is, in the first control mode, during the reference time ΔT, the rotary unit 30 rotates in the first periaxial direction for a first rotation time T1 having the same length as the reference time ΔT. On the other hand, in the second control mode, during the reference time ΔT, the rotary unit 30 rotates in the second periaxial direction for a second rotation time T2 shorter than the first rotation time T1.

As described above, the second rotation time T2 of the rotary unit 30 toward the second periaxial direction during the reference time ΔT in the second control mode is smaller than the first rotation time T1 of the rotary unit 30 toward the first periaxial direction during the reference time ΔT in the first control mode. Therefore, when the first command value S1 during the reference time ΔT in the first control mode and the second command value S2 during the reference time ΔT in the second control mode have the same magnitude, the second rotating speed V2 of the rotary unit 30 in the second control mode and the first rotating speed V1 of the rotary unit 30 in the first control mode have the same magnitude, but the second rotation amount Y2 of the rotary unit 30 during the reference time ΔT in the second control mode is smaller than the first rotation amount Y1 of the rotary unit 30 during the reference time ΔT in the first control mode. Therefore, in this modification, like the first embodiment, the second rotation amount Y2 of the rotary unit 30 during the reference time ΔT provided by the second rotating operation can be smaller than the first rotation amount Y1 of the rotary unit 30 during the reference time ΔT provided by the first rotating operation without performing a speed change operation or the like in addition to the first rotating operation or the second rotating operation.

It is to be noted that, in this modification, the parameter adjustment section 99 can be used to adjust the second rotation time T2 of the rotary unit 30 in the second control mode as long as the second rotation time T2 being smaller than the first rotation time T1.

Furthermore, in the first embodiment, the first command value S1 of the first operation command rises as the movement displacement X1 of the first operation input section 17 from the first input OFF position increases, and the second command value S2 of the second operation command rises as the movement displacement X2 of the second operation input section 18 from the second input OFF position increases, but it is not restricted thereto. For example, as a third modification, such a first operation input section 17 as shown in FIG. 15A may be provided. The first operation input section 17 according to this modification can move to a first input OFF region where the first operation command is not generated and a first input ON region where the first operation command is generated. When the first operation input section 17 moves to the first input ON region, the first rotating operation is input. A region on an arrow G1 direction side of a boundary position B is the first input OFF region, and a region on an arrow G2 direction side of the boundary position B is the first input ON region. FIG. 15B is a view showing a relationship between a movement displacement X'1 of the first operation input section 17 with the boundary position B being a standard and the first command value S1 of the first operation command. As shown in FIG. 15B, in the first input ON region, the first command value S1 which is a command value of the first operation command has a fixed magnitude s0 irrespective of a position of the first operation input section 17. That is, in the first input ON region, the magnitude of the first command value S1 does not change by the movement of the first operation input section 17.

Like the first operation input section 17, the second operation input section 18 can move to a second input OFF region where the second operation command is not generated and a second input ON region where the second operation command is generated. When the second operation input section 18 moves to the second input ON region, the second rotating operation is input. In the second input ON region, the second command value S2 which is a command value of the second operation command has the fixed magnitude s0 irrespective of a position of the second operation input section 18. That is, in the second input ON region, the magnitude of the second command value S2 does not change by the movement of the second operation input section 18.

When the first operation input section 17 is placed in the first input ON region and the second operation input section 18 is placed in the second input OFF position, the first operation command alone is generated. As a result, the control mode switching section 97 switches to the first control mode. On the other hand, when the first operation input section 17 is placed in the first input OFF region and the second operation input section 18 is placed at the second input ON position, the second operation command alone is generated. As a result, the control mode switching section 97 switches to the second control mode.

In this modification, when the first operation input section 17 is placed in the first input ON region throughout the reference time ΔT having a predetermined length, the first rotating speed V1 of the rotary unit 30 has a fixed magnitude v1 throughout the reference time ΔT in the first control mode like in a case where the first command value S1 is set to have the magnitude s0 that is fixed over time in the first embodiment. Further, when the second operation input section 18 is placed in the second input ON region throughout the reference time ΔT, the second rotating speed V2 of the rotary unit 30 has a fixed magnitude v2 throughout the reference time ΔT like in a case where the second command value S2 is set to have the magnitude s0 that is fixed over time in the first embodiment. The magnitude v2 of the second rotating speed V2 of the rotary unit 30 in the second control mode is smaller than the magnitude v1 of the first rotating speed V1 in the first control mode. That is, the second rotating speed V2 of the rotary unit 30 in the second control mode when the second operation input section 18 is placed in the second input ON region during the reference time ΔT is smaller than the first rotating speed V1 of the rotary unit 30 in the first control mode when the first operation input section 17 is placed in the first input ON region during the reference time ΔT (see FIG. 11).

In this case, the second rotation amount Y2 during the reference time ΔT in the second control mode is smaller than the first rotation amount Y1 during the reference time ΔT in the first control mode. Therefore, in this modification, like the first embodiment, the second rotation amount Y2 of the rotary unit 30 during the reference time ΔT provided by the second rotating operation can be reduced to be smaller than the first rotation amount Y1 of the rotary unit 30 during the reference time ΔT provided by the first rotating operation without performing a speed change operation or the like in addition to the first rotating operation or the second rotating operation.

Further, in this modification, like the second modification, during the reference time ΔT in the first control mode, the rotary unit 30 may rotate toward the first periaxial direction for the first rotation time T1 having the same length as the reference time ΔT. Furthermore, like the second modification, during the reference time ΔT in the second control mode, the rotary unit 30 may rotate toward the second periaxial direction for the second rotation time T2 shorter than the first rotation time T1 (see FIG. 14A and FIG. 14B).

As a result, the second rotation time T2 of the rotary unit 30 in the second around-axis direction during the reference time ΔT in the second control mode becomes shorter than the first rotation time T1 of the rotary unit 30 in the first around-axis direction during the reference time ΔT in the first control mode. Therefore, although the second rotating speed V2 of the rotary unit 30 in the second control mode has the same magnitude as the first rotating speed V1 of the rotary unit 30 in the first control mode, the second rotation amount Y2 of the rotary unit 30 during the reference time ΔT in the second control mode is smaller than the first rotation amount Y1 of the rotary unit 30 during the reference time ΔT in the first control mode. Therefore, in this modification, like the first embodiment, the second rotation amount Y2 of the rotary unit 30 during the reference time ΔT provided by the second rotating operation can be smaller than the first rotation amount Y1 of the rotary unit 30 during the reference time ΔT provided by the first rotating operation without performing a speed change operation or the like separately from the first rotating operation or the second rotating operation.

According to the above-described modification, the control mode switching section 97 can switch to the first control mode based on generation of the first operation command by input of the first rotating operation and can switch to the second control mode based on generation of the second operation command by input of the second rotating operation. Furthermore, in the first control mode, the first drive control section 95 may drive and control a drive state of the motor 75 as a drive member in such a manner that the rotary unit 30 can rotate toward the first periaxial direction with the first rotation amount Y1 during the reference time ΔT having the predetermined length. Further, in the second control mode, the second drive control section 96 may drive and control a drive state of the motor 75 in such a manner that the rotary unit 30 can rotate toward the second periaxial direction with the second rotation amount Y2 smaller than the first rotation amount Y1 during the reference time ΔT.

Second Embodiment

A second embodiment according to the present invention will now be described with reference to FIG. 16 and FIG. 17. The second embodiment is provided by modifying the configuration of the first embodiment as follows. It is to be noted that like reference numerals denote parts equal to those in the first embodiment to omit a description thereof.

Figure 16:
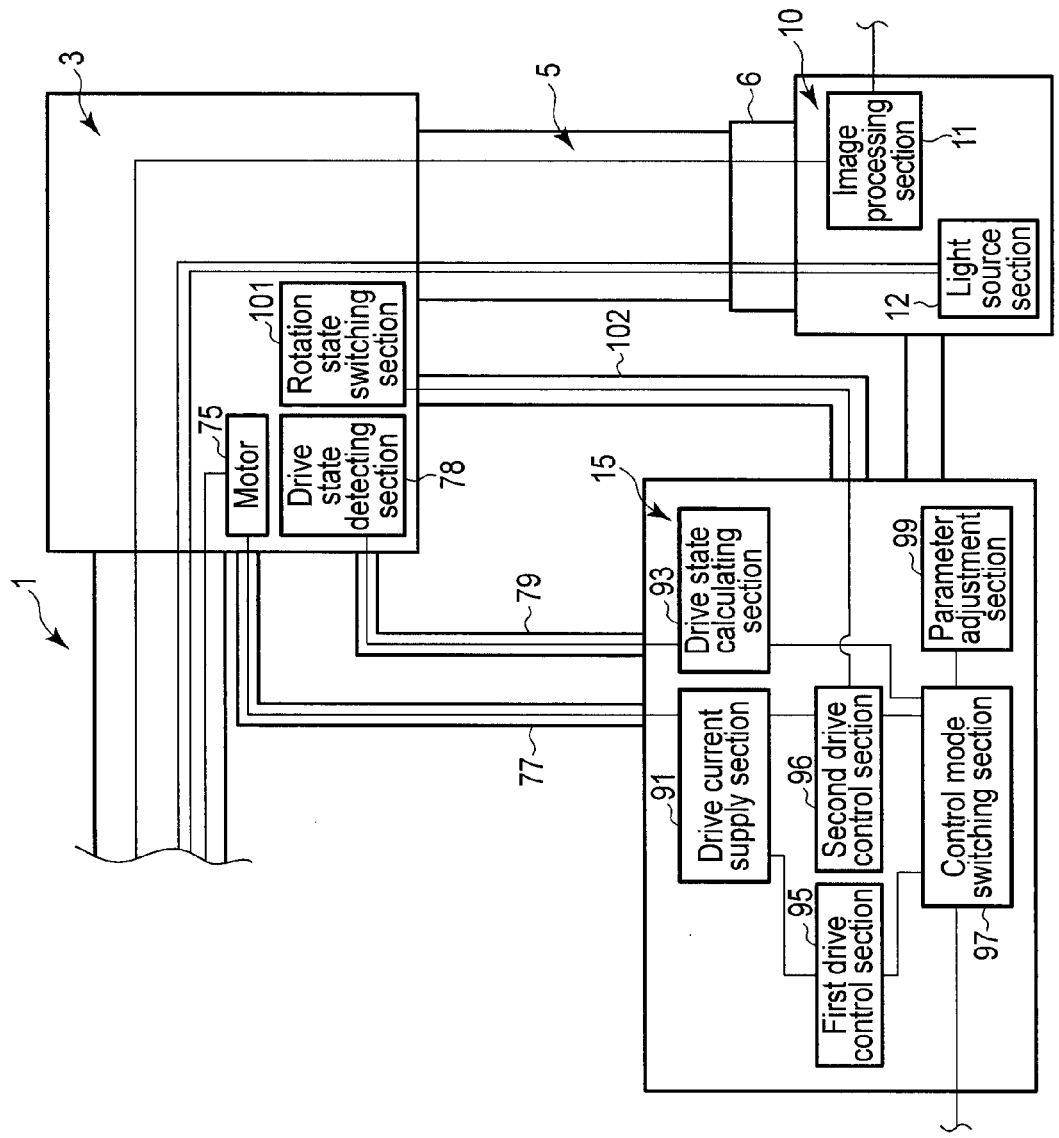
FIG. 16 is a block diagram schematically showing configurations of an operating section, an observation processing unit, and a control unit of an endoscope apparatus according to a second embodiment.

FIG. 16 is a view showing configurations of an operating section 3, an observation processing unit 10, and a control unit 15 in an endoscope apparatus 1 according to this embodiment. As shown in FIG. 16, in the control unit 15, like the first embodiment, a drive current supply section 91, a drive state calculating section 93, a first drive control section 95, a second drive control section 96, and a control mode switching section 97 are provided. However, in this embodiment, differing from the first embodiment, a rotation state switching section 101 such as a rotation state switching button is provided in the operating section 3. In the rotation state switching section 101, a rotation state switching operation for switching a rotation state of a rotary unit 30 toward a second periaxial direction can be input in a second control mode in which the rotary unit 30 rotates in the second periaxial direction. One end of an electrical cable 102 is connected to the rotation state switching section 101. The other end of the electrical cable 102 is connected to the second drive control section 96.

An actuation state of the rotation state switching section 101 changes to an ON state or an OFF state by the rotation state switching operation. In the second control mode, when the rotation state switching section 101 is in the ON state, like the second control mode in the first embodiment, the rotary unit 30 rotates toward the second periaxial direction during a reference time ΔT with a second rotation amount Y2 smaller than a first rotation amount Y1 toward a first periaxial direction in a first control mode. That is, the rotary unit 30 is in a first rotation state in which the rotary unit 30 rotates toward the second periaxial direction with the second rotation amount Y2 during the reference time ΔT.

On the other hand, in the second control mode, when the rotation state switching section 101 is in the OFF state, the rotary unit 30 rotates toward the second periaxial direction during the reference time ΔT with a third rotation amount Y3 larger than the second rotation amount Y2. That is, the rotary unit 30 is in a second rotation state in which the rotary unit 30 rotates in the second periaxial direction with the third rotation amount Y3 during the reference time ΔT.

FIG. 17 is a view showing a method of rotating the rotary unit 30 toward the second periaxial direction in the second control mode. As shown in FIG. 17, in this embodiment, like the first embodiment, when the control mode switching section 97 switches to the second control mode (a step S154), the motor 75 is driven and controlled by the second drive control section 96 (a step S158). Further, the rotary unit 30 is rotated toward the second periaxial direction (a step S159). At this time, whether the rotation state switching section 101 is in the ON state or the OFF state is determined by the second drive control section 96 (a step S165). When the rotation state switching section 101 is in the ON state (the step S165—Yes), the motor 75 is driven to rotate in a second drive direction, thereby rotating the rotary unit 30 toward the second periaxial direction with the second rotation amount Y2 during the reference time ΔT (a step S166). On the other hand, when the rotation state switching section 101 is in the OFF state (the step S165—No), the motor 75 is driven to rotate in the second drive direction, thereby rotating the rotation unit 30 toward the second periaxial direction with the third rotation amount Y3 larger than the second rotation amount Y2 during the reference time ΔT (a step S167).

In the second control mode, the third rotation amount Y3 in the second rotation state during the reference time ΔT is larger than the second rotation amount Y2 in the first rotation state during the reference time ΔT. Therefore, in the second control mode, a third movement amount D3 of an inserting section 2 toward a proximal direction in the second rotation state during the reference time ΔT is larger than a second movement amount D2 toward the proximal direction in the first rotation state during the reference time ΔT. That is, in the second control mode, a movement amount of the inserting section 2 in the proximal direction during the reference time ΔT can be increased by the rotation state switching operation. Therefore, in a case of rapidly removing the inserting section 2 from a lumen 105 without performing observation, mobility of the inserting section 2 toward the proximal direction parallel to a longitudinal axis C can be improved.

Third Embodiment

A third embodiment according to the present invention will now be described with reference to FIG. 18 to FIG. 20. The third embodiment is provided by modifying the configuration of the first embodiment as follows. It is to be noted that like reference numerals denote parts equal to those in the first embodiment to omit a description thereof.

FIG. 18 is a view showing a configuration of a control unit 15 in an endoscope apparatus 1 according to this embodiment. As shown in FIG. 18, in the control unit 15, like the first embodiment, a drive current supply section 91, a drive state calculating section 93, a first drive control section 95, a second drive control section 96, and a control mode switching section 97 are provided. However, in this embodiment, differing from the first embodiment, a mode switching state setting section 111 is provided in the control unit 15. The mode switching state setting section 111 is electrically connected to the control mode switching section 97. Moreover, in the control unit 15, a third drive control section 112 and a fourth drive control section 113 are provided. The third drive control section 112 and the fourth drive control section 113 are electrically connected to the control mode switching section 97 and the drive current supply section 91. In the mode switching state setting section 111, a switching state of a control mode in the control mode switching section 97 is set.

The mode switching state setting section 111 can set a switching state of a control mode in the control mode switching section 97 to a first switching state and a second switching state. In the first switching state, when a first operation command is generated by a first rotating operation, the control mode switching section 97 switches to a first control mode in which the first drive control section 95 drives and controls a motor 75. As a result, like the first embodiment and the modifications described above, a rotary unit 30 rotates toward a first periaxial direction with a first rotation amount Y1 during a reference time ΔT. Further, in the first switching state, when a second operation command is generated by a second rotating operation, the control mode switching section 97 switches to a second control mode in which the second drive control section 96 drives and controls the motor 75. As a result, like the first embodiment and the modifications described above, the rotary unit 30 rotates toward a second periaxial direction with a second rotation amount Y2 smaller than the first rotation amount Y1 during the reference time ΔT. Furthermore, in the first switching state, when the first operation command and the second operation command are not generated, the motor 75 is stopped, and rotation of the rotary unit 30 is stopped.

In the second switching state, when the second operation command is generated by the second rotating operation, like the first switching state, the current mode is switched to the second control mode. However, in the second switching state, when the first operation command and the second operation command are not generated, the current mode is switched to a third control mode in which the third drive control section 112 drives and controls the motor 75. Moreover, in the second switching state, when the first operation command is generated, the current mode is switched to a fourth control mode in which the fourth drive control section 113 drives and controls the motor 75.

In the third control mode, the third drive control section 112 drives and controls a drive state of the motor 75 in such a manner that the rotary unit 30 rotates toward the first periaxial direction. In the third control mode, since the first operation command is not generated, a first command value S1 of the first operation command is zero. FIG. 19 is a view showing a change with time of a first rotating speed V1 of the rotary unit 30 in the first around-axis direction in the third control mode. As shown in FIG. 19, in the third control mode, the first rotating speed V1 of the rotary unit 30 has a magnitude v1 that is constant over time:

In the fourth control mode, the fourth drive control section 113 drives and controls a drive state of the motor 75 in such a manner that the rotary unit 30 rotates toward the first periaxial direction. In the fourth control mode, the first operation command is generated. Like the first embodiment, as a movement displacement X1 of a first operation input section 17 from a first input OFF position increases, a first command value S1 of the first operation command rises. FIG. 20 is a view showing a relationship between the first command value S1 of the first operation command and a magnitude of the first rotating speed V1 of the rotary unit 30 toward the first periaxial direction. As shown in FIG. 20, in the fourth control mode, as the first command value S1 of the first operation command increases, the first rotating speed V1 of the rotary unit 30 decreases. Additionally, when the first operation input section 17 moves to a first maximum input position and the first command value S1 has a magnitude s0, a magnitude of the first rotating speed V1 of the rotary unit 30 becomes zero. As a result, the rotation of the rotary unit 30 stops.

In this embodiment, a switching state of the control mode in the control mode switching section 97 can be set in accordance with a use state of the endoscope apparatus 1 and a preference of an operator.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An insertion apparatus comprising:
   an inserting section which is extended from a proximal direction toward a distal direction along a longitudinal axis;
   a rotary unit which includes a spiral fin portion spirally extended around the longitudinal axis, and which is provided to an outer peripheral direction side of the inserting section in a state that the rotary unit is rotatable toward a first periaxial direction around the longitudinal axis and a second periaxial direction opposite to the first periaxial direction with respect to the inserting section;
   a drive member which is configured to generate a drive force of rotating the rotary unit;
   an operation unit which is configured to generate a first operation command based on an input of a first operation of rotating the rotary unit toward the first periaxial direction, which is configured to generate a second operation command based on an input of a second operation of rotating the rotary unit toward the second periaxial direction;
   a first drive control section which is configured to drive and control a drive state of the drive member in the first control mode based on generation of the first operation command in such a manner that the rotary unit rotates toward the first periaxial direction, the first drive control section being configured to adjust a first rotation amount during a reference time having a predetermined length or a first current amount of a current supplied to the drive member during the reference time in accordance with a first command value, which is a command value of the first operation command; and
   a second drive control section which is configured to drive and control the drive state of the drive member in the second control mode based on generation of the second operation command in such a manner that the rotary unit rotates toward the second direction, the second drive control section being configured to adjust a second rotation amount during the reference time or a second amount of the current supplied to the drive member during the reference time in accordance with a second command value, which is a command value the second operation command, the first drive control section and the second drive control section being configured to adjust the second rotation amount in the second control mode to be smaller than the first rotation amount in the first control mode or to adjust the second amount of the current in the second control mode to be smaller than the first amount of the current in the first control mode when the first command value and the second command value are set to have the same magnitude.

2. The insertion apparatus according to claim 1, further comprising a control mode switching section which is configured to switch to the first control mode based on the generation of the first operation command, and which is configured to switch to the second control mode based on the generation of the second operation command.

3. The insertion apparatus according to claim 1,
   wherein the first drive control section is configured to drive and control the drive member in such a manner that a first rotating speed of the rotary unit toward the first periaxial direction increases as the first command value rises in the first control mode, and the second drive control section is configured to drive and control the drive member in such a manner that a second rotating speed of the rotary unit toward the second periaxial direction increases as the second command value rises in the second control mode.

4. The insertion apparatus according to claim 3,
wherein the first drive control section is configured to drive and control the drive member in such a manner that the first rotating speed of the rotary unit is proportionate to the first command value of the first operation command at a first ratio in the first control mode, and the second drive control section is configured to drive and control the drive member in such a manner that the second rotating speed of the rotary unit is proportionate to the second command value of the second operation command at a second ratio smaller than the first ratio in the second control mode.

5. The insertion apparatus according to claim 1,
wherein, in the first control mode, the first drive control section is configured to drive and control the drive member in such a manner that a first rotating speed of the rotary unit toward the first periaxial direction has a fixed magnitude throughout the reference time, and in the second control mode, the second drive control section is configured to drive and control the drive member in such a manner that a second rotating speed of the rotary unit toward the second periaxial direction has a fixed magnitude throughout the reference time and becomes lower than the first rotating speed during the reference time in the first control mode.

6. The insertion apparatus according to claim 1,
wherein, in the first control mode, the first drive control section is configured to drive and control the drive member in such a manner that a first rotating speed of the rotary unit toward the first periaxial direction has a fixed magnitude through the reference time, and in the second control mode, the second drive control section is configured to drive and control the drive member in such a manner that the rotary unit intermittently rotates toward the second periaxial direction throughout the reference time and a second rotating speed of the rotary unit has the same magnitude as the first rotating speed during the reference time in the first control mode.

7. The insertion apparatus according to claim 1, further comprising a switching section configured to input a switching operation of switching a rotation state of the rotary unit toward the second periaxial direction in the second control mode, wherein, in the second control mode, the second drive control section is configured to change the drive state of the drive member based on the switching operation by the switching section, the second drive control section being configured to rotate the rotary unit toward the second periaxial direction in a first rotation state in which rotation is performed during the reference time with the second rotation amount or a second rotation state in which rotation is performed during the reference time with a third rotation amount larger than the second rotation amount.

8. The insertion apparatus according to claim 1,
wherein the operation unit includes:
a first movable portion which is movable based on the input of the first operation between a first input OFF position at which the first operation command is not generated and a first maximum input position at which the first command value becomes maximum, the first command value of the first operation command being increased as a movement displacement of the first movable portion from the first input OFF position rises; and a second movable portion which is movable based on the input of the second operation between a second input OFF position at which the second operation command is not generated and a second maximum input position at which the second command value becomes maximum, the second command value of the second operation command being increased as a movement displacement of the second movable portion from the second input OFF position rises.

9. The insertion apparatus according to claim 1,
wherein the operation unit includes:
a first movable portion which is movable based on the input of the first operation between a first input OFF region where the first operation command is not generated and a first input ON region where the first operation command is generated, the first command value of the first operation command being fixed when the first movable portion is in the first input ON region irrespective of a position in the first input ON region; and a second movable portion which is movable based on the input of the second operation between a second input OFF region where the second operation command is not generated and a second input ON region where the second operation command is generated, the second command value of the second operation command being fixed when the second movable portion is in the second input ON region irrespective of a position in the second input ON region.

10. The insertion apparatus according to claim 1, further comprising a drive force transmitting unit which is configured to transmit the drive force generated by the drive member to the rotary unit, the drive force transmitting unit being configured to allow a first propulsive force toward the distal direction to act on the inserting section and the rotary unit by rotating the rotary unit toward the first periaxial direction in a pressing state in which a pressing force acts on the spiral fin portion toward an inner peripheral direction, the drive force transmitting unit being configured to allow a second propulsive force toward the proximal direction to act on the inserting section and the rotary unit by rotating the rotary unit toward the second periaxial direction in the pressing state.

* * * * *